(12) United States Patent
Hartland

(10) Patent No.: US 10,495,621 B2
(45) Date of Patent: Dec. 3, 2019

(54) APPARATUS AND METHOD FOR SURVEYING

(71) Applicant: Martin John Hartland, Houston, TX (US)

(72) Inventor: Martin John Hartland, Houston, TX (US)

(*) Notice: Subject to any disclaimer, the term of this patent is extended or adjusted under 35 U.S.C. 154(b) by 240 days.

(21) Appl. No.: 14/766,390

(22) PCT Filed: Feb. 6, 2013

(86) PCT No.: PCT/IB2013/000341
§ 371 (c)(1),
(2) Date: Aug. 6, 2015

(87) PCT Pub. No.: WO2014/122494
PCT Pub. Date: Aug. 14, 2014

(65) Prior Publication Data
US 2015/0377852 A1    Dec. 31, 2015

(51) Int. Cl.
*G01V 1/38* (2006.01)
*G01N 33/18* (2006.01)
*B63B 21/56* (2006.01)
*B63B 21/66* (2006.01)

(52) U.S. Cl.
CPC ......... *G01N 33/1886* (2013.01); *B63B 21/56* (2013.01); *B63B 21/66* (2013.01); *G01V 1/3817* (2013.01); *G01V 1/3826* (2013.01); *G01V 1/3843* (2013.01)

(58) Field of Classification Search
None
See application file for complete search history.

(56) References Cited

U.S. PATENT DOCUMENTS

| 3,560,912 | A | * | 2/1971 | Malone et al. | ........... | B63G 8/42 |
|  |  |  |  |  |  | 114/245 |
| 3,896,756 | A | * | 7/1975 | Pearson | ................. | B63B 21/66 |
|  |  |  |  |  |  | 114/245 |
| 4,350,111 | A | * | 9/1982 | Boyce, II | ................. | B63G 8/18 |
|  |  |  |  |  |  | 114/245 |
| 4,617,518 | A | * | 10/1986 | Srnka | ....................... | G01V 3/06 |
|  |  |  |  |  |  | 324/364 |

(Continued)

FOREIGN PATENT DOCUMENTS

EP    0 154 968 A2    9/1985
FR    2 496 277 A1    6/1982

(Continued)

*Primary Examiner* — Jill E Culler
(74) *Attorney, Agent, or Firm* — Birch, Stewart, Kolasch & Birch, LLP

(57) ABSTRACT

An apparatus for surveying includes at least one survey cable, each survey cable having a proximal end attached to a mother vessel, a distal end connected to at least one subsurface towing vessel, and at least one survey device connected to the survey cable between the proximal end and the distal end. The survey cable extends in a direction perpendicular to a longitudinal axis of the mother vessel during a survey. The survey cables extend a distance E sideways from the mother vessel, for example under an ice cap, e.g. solid ice or ice floes. When surveying in a polar region, the mother vessel needs only to break a narrow channel in order to survey a large area, thus saving energy, time and money.

8 Claims, 3 Drawing Sheets

(56) References Cited

U.S. PATENT DOCUMENTS

| | | | | |
|---|---|---|---|---|
| 4,890,568 | A * | 1/1990 | Dolengowski | B63B 21/66 114/163 |
| 5,913,280 | A * | 6/1999 | Nielsen | G01V 1/3826 114/242 |
| 6,234,102 | B1 * | 5/2001 | Russell | B63B 21/66 114/253 |
| 6,267,070 | B1 | 7/2001 | Russell et al. | |
| 6,285,956 | B1 * | 9/2001 | Bennett | B63B 21/66 702/14 |
| 6,606,958 | B1 * | 8/2003 | Bouyoucos | B63B 21/66 114/242 |
| 7,793,606 | B2 * | 9/2010 | Olivier | G01V 1/3826 114/245 |
| 8,183,868 | B2 * | 5/2012 | Summerfield | G01V 3/083 324/334 |
| 9,126,661 | B2 * | 9/2015 | McKey, III | B63B 21/66 |
| 2010/0226204 | A1 | 9/2010 | Gagliardi et al. | |
| 2012/0300581 | A1 * | 11/2012 | Vahida | G01V 1/3817 367/16 |

FOREIGN PATENT DOCUMENTS

| | | |
|---|---|---|
| WO | WO 98/24685 A1 | 6/1998 |
| WO | WO 99/12055 A1 | 3/1999 |

* cited by examiner

APPARATUS AND METHOD FOR SURVEYING

BACKGROUND

Field of the Invention

The present invention concerns an apparatus and a method for surveying at sea, in particular in a polar region under an ice cap.

Prior Art

Conventional seismic surveying at sea involves towing an array of cables, called streamers, behind a ship. The streamers are typically aligned parallel to each other, for example with a distance 25, 50 or 100 meters between each streamer, and they comprise at least one acoustic source capable of generating acoustic waves intended to propagate into a formation below the seabed, where the waves are reflected by different rock strata at different depths. The acoustic source is usually one or more airguns, but explosive charges or other signal sources are also known in the art.

FIGS. 4a and 4b are schematic views of an acoustic signal source.120' with one or more airguns 440 arranged in clusters 44, which in turn are arranged in an array 450. The airguns 440 are supplied with pressurized air through lines 420. Each airgun may typically have a volume of 0,3-9,8 litres (20-600 in$^3$), and a typical array may total up to about 50 litres (3000 in$^3$). Each airgun in the array is charged with pressurized air through lines 420. Typical pressures are in the range 138-207 bar (2000-3000 psi). The air is released abruptly to create acoustic source waves. The characteristics of the source will be input to a mathematical model at a later stage. Optional shields 430, e.g. stainless steel plates, may be provided to protect a buoyancy element 410 from the full impact of the strong pulse generated when airguns are fired. The shields 430 and/or buoyancy element 410 must be able to withstand repeated loads as the airguns are fired at predetermined intervals during a seismic survey. Several seismic sources with some or all of the features above are available. Well proven sources are valuable due to the design, testing and adaptations required to make them work properly.

The reflected acoustic waves, or echoes, are received by acoustic receivers and recorded for further analysis. FIG. 3a schematically shows a grid on a seabed, where measuring points are spaced apart a distance X in one direction, and Y in a perpendicular direction. The devices 300 can be simple acoustic receivers or self contained nodes, each node comprising a receiver, a recorder and/or a power source. A full node is more expensive than a receiver, and the distances X, Y in a current array typically vary from 6.5 m between receivers to 300 m between full nodes. FIG. 4b is a side view of a cable 301 on the seabed. The receivers 302 are connected via the cable 301 to a common recorder 303, and the distance between the receivers may be as low as 6.5 m using current techniques for seismic surveying. Several alternative embodiments are known, for example receivers on the streamers, different types of receivers or nodes, etc. Selecting the equipment and where to deploy it is left to the skilled person.

The arrays in FIG. 3a and FIG. 3b are disposed on the seabed by a Remotely Operated Vehicle (ROV). Normally, there are at least two ROVs aboard a surveying ship for this purpose. A typical ROV is powered and/or controlled through a cable known as a 'tether'. The tether extends from a mother vessel via a Tether Management System (TMS) to the interior of the ROV. The ROV may, for example, have one or two thrusters or propellers that are able to rotate about an axis perpendicular to the thrust force, and thus provide a thrust force having an adjustable angle relative to the body of the ROV. An ROV is standard equipment, and any suitable ROV can be used with the present invention.

In an entirely different type of survey, bathymetry, a side scan sonar can be used to provide signals that are echoed from the seabed. The signals are typically received, recorded and analyzed to map the topography of the seabed. Further, the signal sources and/or detectors may have known characteristics adapted to the mathematical models used for analysis.

In other types of survey, measurements may be taken at known points in space to map electro magnetic resistance, salinity, location and velocity of an ocean current, or any other parameter of interest.

In general, developing and testing equipment for use at sea is relatively expensive, and hence it is desirable to select well proven tools for use in a survey. However, selecting the actual equipment and techniques for measuring the parameters of interest is left to the skilled person.

Many of the known methods for surveying involve towing equipment at the surface of the sea, for example by providing a buoyancy element such as the element 410 in FIG. 4a, with sufficient positive buoyancy to keep the entire assembly 120' floating.

However, towing equipment at or near the surface of the sea can be a problem in a polar region, where the water can be covered by solid ice or small and large pieces of ice may be floating in the water. For simplicity, the term 'ice cap' is used in the following description and claims to denote any solid ice, large and small ice floes and more or less broken ice floating in the water.

For surveying ice covered water, it has been proposed to use an icebreaker as a mother vessel in the survey. This causes new problems. For example, the propeller(s) and/or contact between the ice and the hull may induce noise in the acoustic signals of a seismic or bathymetric survey.

In order to prevent the noise from icebreaking from disturbing the signals, NO169743B proposes to use a conventional icebreaker as a towing vessel for a streamer cable, and stop the icebreaker during active survey. The streamer cable is hauled in with a speed corresponding to the desired propulsion speed of the cable during detection. After detection, the vessel again resumes ordinary operational speed, and the streamer is paid out with a speed which maintains the desired advancing speed of the system.

Further, using an icebreaker to create a passage for a single streamer cable towed behind the vessel can necessitate many passages through the ice to obtain a desired resolution in the survey. This, in turn, requires energy for breaking ice, and hence leads to a more expensive survey. Breaking ice for a vessel towing an array of several, parallel streamer cables implies added cost in a similar manner.

Still further, the time available from the ice breaks to the water refreezes may be short, and thus limit the time available for a conventional survey. Other problems associated with towing a cable through water with partly broken ice, include, for example, the risk for a cable being unintentionally deviated from its intended course, or even broken, by a floating piece of ice, e.g. an ice floe.

Similar problems are encountered in other surveys in polar regions, for example surveys using side scan sonar for bathymetry or electro magnetic resistance surveys.

WO 9912055 A1 og WO 9824685 A1 disclose other apparatuses and methods wherein streamers are towed behind a mother vessel.

US 2010226204 A1 discloses a method for seismic surveying wherein several parallel streamers are towed behind a mother vessel. Autonomous or remotely controlled vehicles can be attached to the distal ends of the streamers, such that the streamers can be controlled individually in a lateral and vertical direction. The streamers can be towed under ice and debris floating on the surface. Features from US2010226204 A1 appear in the preambles of the independent claims.

Surveying under an ice cap, e.g. solid ice or ice floes, still poses the problems discussed above, for example requiring breaking ice in order to tow the streamers behind the mother vessel.

Thus, an objective for the present invention is to solve at least one of the problems above, while using as much as possible of well proven techniques and equipment.

SUMMARY OF THE INVENTION

An apparatus for surveying comprises at least one survey cable, each survey cable having a proximal end attached to a mother vessel, a distal end connected to at least one subsurface towing vessel, and at least one survey device connected to the survey cable between the proximal end and the distal end. The apparatus is distinguished in that the survey cable extends in a direction perpendicular to a longitudinal axis of the mother vessel during a survey.

In another aspect, the invention concerns a method for surveying. In particular the method comprises the steps of attaching at least one survey cable to a mother vessel, connecting a distal end of each survey cable to at least one subsurface towing vessel and connecting at least one survey device to the survey cable between the proximal end and the distal end, The method is further distinguished by deploying the survey cable in a direction perpendicular to a longitudinal axis of the mother vessel and obtaining a measurement using the survey device.

The mother vessel can be an icebreaker breaking a relatively narrow channel through an icecap, or a submarine moving below the ice. In either case, when subsurface towing vessels tow the survey cable under the ice, the energy, time and expenses associated with icebreaking are expected to be substantially reduced. Further, equipment that is already present on the mother vessel may be used without modification, or easily adapted for use with the present invention. This may include using one or more ROVs already present on the mother vessel to tow the survey cable, and/or providing adjustable buoyancy to well proven equipment. Such equipment should preferably have near neutral buoyancy for subsea deployment, and positive buoyancy in order to float on the surface if surveying in open water.

Other features and advantages appear in the accompanying dependent claims.

BRIEF DESCRIPTION OF THE DRAWINGS

The invention will be further explained in the following detailed description with reference to the accompanying drawings, in which.

DETAILED DESCRIPTION

The drawings are only intended to illustrate the principles of the invention. They are not to scale, and numerous details are omitted for the sake of clarity.

Figure 1:
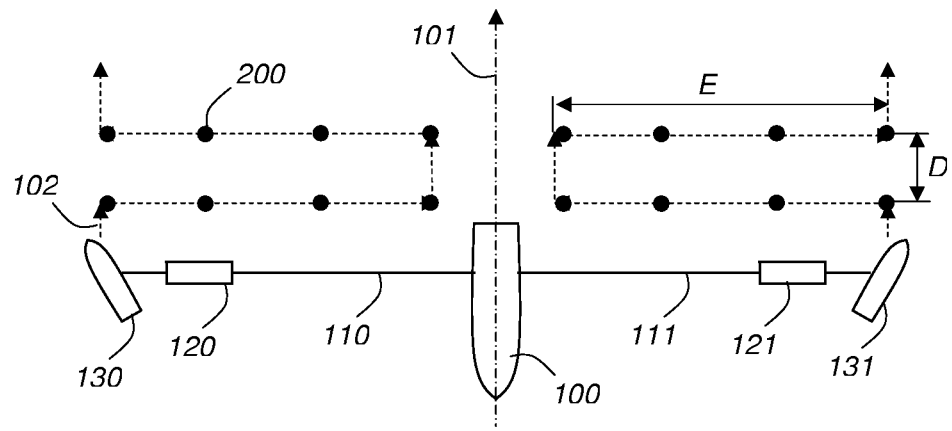
FIG. 1 is a schematic view of an apparatus according to the invention.
Figure 5:
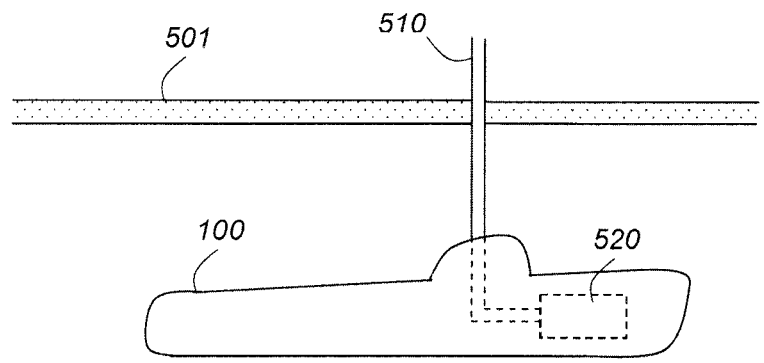
FIG. 5 shows an alternative embodiment where the mother vessel is a submarine.

Referring now to the drawings, FIG. 1 shows a mother vessel 100 moving slowly along its longitudinal axis 101 in the direction indicated by an arrow. The mother vessel can be, for example an icebreaker as illustrated in FIG. 1 or a submarine as shown in FIG. 5. Current icebreakers tend to use their propellers to break the ice, and hence the mother vessel is depicted as moving backwards, i.e. stern first. However, a mother vessel may of course also move with its bow pointing in the direction indicated by the arrow.

Two survey cables 110, 111 extend from the mother vessel 100. One or more than two cables may be employed. The maximum extension E is determined by the length of the survey cable and other factors, for example the length of a tether connecting an ROV with the mother vessel. Currently, the maximum extension is about 1500 m and rising. 3 km appears to be within reach of today's technology.

Figure 4A:
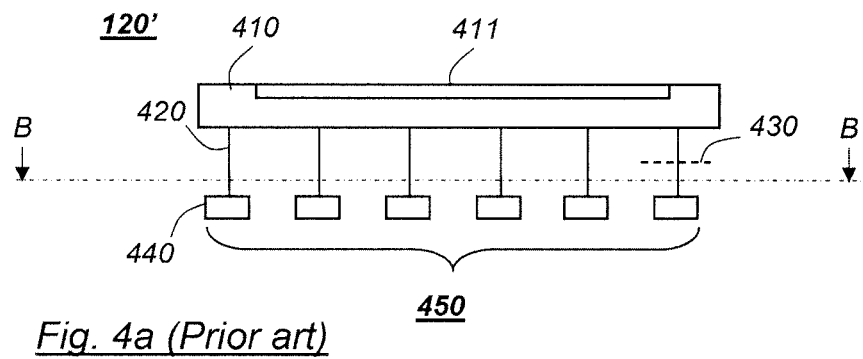
FIG. 4 is a schematic view of a conventional seismic signal source.
Figure 4B:
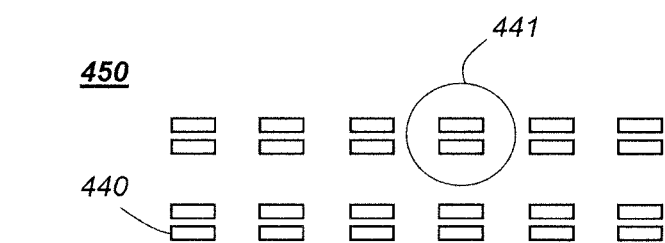

At least one survey device 120, 121 is connected to each survey cable 110, 111. The survey device can be any signal source, receiver, recorder or other detector for measuring a signal or parameter of interest. An airgun array as shown in FIGS. 4a and 4b and discussed above is merely one example. As noted above, the signal source may alternatively be a side scan sonar for bathymetry, a device used in an electromagnetic resistance survey, or any other signal source known in the art. Further, the survey device can be a receiver or detector of any conceivable signal, including acoustic and electromagnetic signals ranging from gamma-wavelengths, through visible light, to microwaves and beyond. The term 'detector' in the claims is intended to include any device for measuring a parameter of interest, for example receivers, recorders, probes and devices for measuring pressure, temperature, salinity, pH, water velocity, etc. The nature of the survey device itself, i.e. the signal source and/or detector, is not part of the invention.

The distal end of cable 110, i.e. the end that is furthest away from the mother vessel 100 during operation, is connected to at least one subsurface towing vessel 130. For example, two or more ROVs may be required to handle the forces from one survey cable 110 or 111. For simplicity, the at least one ROV or other subsurface towing vessel is referred to as 'the subsurface towing vessel' in the following. The subsurface towing vessel 130 works by extending cable 110 from the vessel, wherein the cable is connected at a proximal end.

In the schematic FIG. 1, the cable is extended in a first direction perpendicular to the longitudinal axis 101 of the mother vessel and away from the vessel. Signals are provided or measurements performed at predetermined points 200. For consistency with existing surveying models, the distance D between the horizontal rows of point 200 may correspond to the distance between conventional parallel streamers, e.g. 25, 50 or 100 m. Further, the distance between points 200 may correspond to the intervals at which the airguns would be fired in a conventional survey.

In reality, the survey cable may arch due to drag or buoyancy, and the actual direction may very well deviate from the 90° angle shown in FIG. 1. In principle, the curvature and direction of the cable is not important as long as the source signals are provided and/or measurements are taken at the predetermined spots 200. However, for practical reasons it may be desirable to keep the cable as straight as possible, and as near perpendicular to the longitudinal axis as possible. It is also noted that any lateral motion from the mother vessel will have a component in the direction perpendicular to the longitudinal axis. The term 'first direction' of the independent claims should be construed as this perpendicular component, and thus includes any lateral movement away from the mother vessel. In ice covered water, the lateral motion is intended to bring the survey cable with its survey device under an icecap, for example beside a narrow channel created by an icebreaker.

In a similar manner, the direction opposite the first direction is also shown at right angles to the longitudinal axis 101, and should be construed as the component perpendicular to the longitudinal axis 101 of the actual motion.

To prevent the cable from imposing an unnecessary or excessive force on the subsurface towing vessel, the cable and its survey device may be provided with near neutral buoyancy. This is discussed below with reference to FIG. 4.

A neutral cable towed by two vessels attached to opposite ends of the cable will tend to arch backwards due to drag forces. Similar drag may be imposed by underwater currents. It is left to the skilled person to provide suitable means for reducing drag, for example in the form of a foil shaped cable cross-section.

A second cable 111 is connected in a similar manner to a second subsurface towing vessel 131, which may operate on the other side of the mother vessel 100.

In one embodiment, each cable may be spooled onto a rotary drum, e.g. a winch drum, on the mother vessel 100. When the subsurface towing vessel moves away from the mother vessel, such a drum may rotate slowly in one rotary direction and act as a brake in order to keep the cable as tensioned as possible without risking that the cable break. Similarly, the rotary drum may rotate in the other direction to haul in the cable. In this case, the subsurface towing device acts as brake, and provides a suitable tension in the cable.

The survey cable 110, 111 may comprise a power line for providing power to equipment connected to the cable, i.e. survey devices 120, 121 and/or subsurface towing vessels 130, 131.

In one embodiment, the power line is a tube or pipe used for conducting a compressed gas, for example high-pressure air. Compressed gas can release a comparatively large amount of energy in a relatively short time, which by definition is high power. Hence, a power line for compressed gas is a preferred means for conveying power in some applications, for example for firing an airgun. A power line used for conveying compressed gas may be manufactured from a reinforced polymer or metal as known in the art.

In another embodiment, the power line is a tube or pipe used for conducting a hydraulic liquid. As known in the art, hydraulic power is useful when a large force is required. A hydraulic power line may be employed instead of, or in addition to, a power line for compressed gas. A hydraulic power line may also be manufactured from a reinforced polymer or metal as known in the art.

In yet another embodiment, the power line is an electrical conductor used for conducting electric power.

Any combination of power lines conveying compressed gas, hydraulic power or electric power is anticipated by the present invention. Several designs, tubes and combinations are commercially available, and can be used in the present invention. The choice of types and combinations of power lines depends on the application, and is left to the skilled person.

A cable comprising one or more power lines is known in the art as an umbilical. It is well known how to determine a suitable least diameter for a drum in order to prevent tubing inside the umbilical from floating due to excessive bending.

An umbilical cable may also comprise a communications line providing communication between the mother vessel 100 and the equipment 120, 121, 130, 131 connected to the cable. Typical communication transmitted over a communications line include control signals for the devices and/or towing vessels and measurement signals or feedback from the equipment to the mother vessel 100.

The subsurface towing vessel can be a specially designed vessel or a conventional remotely operated vehicle (ROV). A typical ROV is controlled through an umbilical known as a tether, and is used to dispose hydrophones and other equipment on the seabed for seismic surveys and other applications. The ROV and its tether are designed to withstand pressures on the seabed, and is thus likely to withstand the shockwaves from an airgun. The tether can have neutral buoyancy, cf. the discussion above. The ROV can typically also provide sufficient force to tow a survey cable as required by the present invention, and may be used as a subsurface towing vessel as specified herein. If one ROV can be used for both purposes, the cost of operation is expected to decrease.

For the sake of order it is emphasized that the tether in general is a separate cable and different from the survey cable disclosed above. A standard tether may currently be up to 800 meters long, and may limit the maximum extension of the survey cable accordingly.

The method for using the equipment disclosed above is illustrated in FIG. 1. The dash-dot line 101 illustrates the movement of the mother vessel 100 and the dotted lines illustrate possible paths for the subsurface towing vessels 130 and 131.

In FIG. 1 the subsurface towing vessel 130 has pulled the survey device 120 connected to survey cable 110 sideways away from mother vessel 100. During the towing, the survey device 120 may have conducted measurements continuously, or as in seismic surveys, at discrete points 200. When the survey cable is extended to its maximum length, which may or may not correspond to a tether length of 800 meters, the vessels advances a predetermined distance D, which may correspond to the distance between streamers in a conventional seismic survey. Then the subsurface towing device 130 is pulled back towards the mother vessel 130 as indicated by the dotted line 102. In this phase, the subsurface towing vessel may act as a brake, and the survey device 120 may perform a number of measurements as indicated by discrete measuring points 200.

Once the subsurface towing vessel is pulled back to a minimum distance from the mother vessel 100, both vessels advance a predetermined distance in the direction indicated by arrow 101, and the sequence is repeated. A similar dotted line with discrete measuring points illustrates a path for the second subsurface towing vessel 131 providing a tensioning force on survey cable 111.

Drag on the cables will generally cause the real path to deviate from the schematic paths shown in FIG. 1. Further, it is emphasized that measurements may be performed while the mother vessel 100 advances continuously, and thus that the stops indicated by the square forms of the dotted lines are optional.

The inventive idea is to use subsurface towing vessels to extend a survey cable sideways from a mother vessel. From prior art it is known to drag the survey cable behind the mother vessel. As any movement in a plane can be decomposed into a component along the longitudinal axis of the mother vessel and an axis perpendicular to said axis, it should be understood that the distal end of a survey cable 110 can be towed along any desired path around the mother vessel 100, for example in circular, rectangular or helical forms. Again, the vessels 100 and 130, 131 may advance steadily or stop at certain intervals to obtain measurements.

Figure 2:
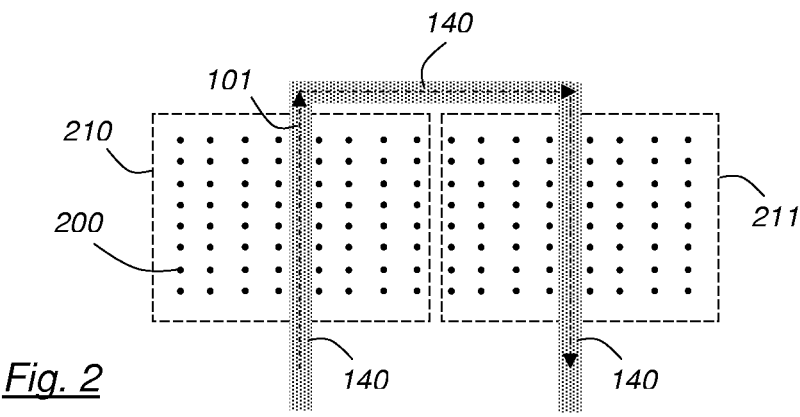
FIG. 2 is a schematic view of a possible survey pattern.

FIG. 2 is a schematic view of a path 140 a mother vessel might follow using the method discussed above. Imagine the mother vessel 100 breaking a narrow channel through an icecap and sending a subsurface towing vessels to each side under an icecap. On the first leg, in the direction toward the top of the drawing, a survey cable fires an airgun or performs some measurement at each discrete point 200, surveying a field 210. Continuing the example with an ROV run on a tether up to 800 meters, the field 210 surveyed on the first leg might be up to 1.6 km wide.

Once the field 210 is surveyed, the mother vessel turns around as illustrated by the horizontal leg of path 140 in FIG. 2, to surveys a second field 211 while moving in the opposite direction of the first leg. Continuing the numerical example, the second field 211 might also be 1.6 km wide, and the first and second legs might be parallel narrow channels 1.6 km apart.

As discussed above, the mother vessels may tow the survey cable in any direction, and follow any path around the ship within a distance determined by the survey cable and, in the case of an ROV run on its tether, the length of the tether. With current available equipment, both lengths can be shorter or longer than the 800 meters in the example above.

The mother vessel may move continuously during the survey, or it might stop at predetermined intervals, for example in order to make the survey cable travel as straight as possible during a series of measurements. Hence, the pattern of points 200 may vary from the one shown in FIG. 2.

In either case, the energy required to break widely spaced narrow channels is substantially less than the energy required to break all ice in, for example, the fields 210 and 211 in FIG. 2.

Further, the subsurface towing vessels and the survey cable can be submerged to a depth where there are little or no obstacles. Hence, problems arising from towing cables through more or less broken ice are solved.

Figure 3A:
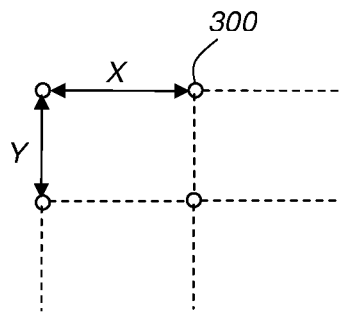
FIG. 3 is a schematic view of seismic detector arrays disposed by an ROV.
Figure 3B:
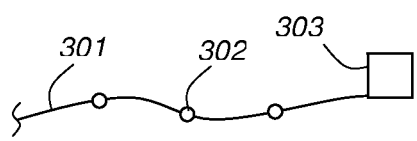

FIG. 3 (prior art) was described in the introduction.

FIG. 4a shows a conventional airgun array 120' with a device 411 providing variable buoyancy for buoyancy control.

Typical parts of a conventional airgun assembly are briefly described in the introduction with reference to FIG. 4. FIG. 4a shows a fixed volume buoyancy 410, which is typically a plastic pipe with walls that are sufficiently thick to withstand the shock from the airguns. Lines 420 provide compressed air and control signals to the airguns, and shields 430 may optionally protect the buoyancy elements from the pressure shock when the airguns are fired. In FIG. 4a, one shield is indicated by a dotted line to illustrate that it is optional. Shields 430 may be provided at all lines 420 or along the entire array if desired.

FIG. 4b depicts an array of airguns as viewed from the plane B-B in the direction indicated by arrows. The schematic drawing is intended to illustrate that individual airguns may be assembled in clusters 441, and that the clusters are further arranged into an array 450.

The fixed buoyancy element 410 is normally designed to keep the airgun array floating. However, in the present application, neutral buoyancy is desired. To illustrate, Archimedes' principle may be stated in terms of forces:

Any object, wholly or partially immersed in a fluid, is buoyed up by a force equal to the weight of the fluid displaced by the object Using common terms in the art, 'positive buoyancy' means that a net upward force is acting on a submersed object. Similarly, 'negative buoyancy' means that a net downward force acts on the object. The object has 'neutral buoyancy' or is 'neutral' if it is buoyed up by a force that is equal to the weight of the object.

In the present application, the aim is to provide a signal or perforin a measurement at predetermined spots 200 as discussed with reference to FIG. 1. If the survey cable 110, 111 and/or its survey device have significant positive or negative buoyancy, the subsurface towing vessel might have to provide an extra force to keep the actual position of the survey device reasonably close to the predetermined spot 200, cf. FIG. 1. Hence, the cable with its survey device(s) should preferentially have near neutral buoyancy. To achieve this, a conventional floating cable or piece of equipment, for example the survey device 120, can be provided with added weight (not shown in FIG. 4) to make it slightly negative, and a variable gas filled volume for buoyancy control. In practice, a buoyancy control device might be connected to the variable volume, and vary the volume depending on a measured ambient pressure representing depth, and a preset value for the desired depth. Such a buoyancy control device might advantageously also learn not to compensate for changes in depth immediately after an airgun is released.

The buoyancy system thus comprises a fixed volume 410 that essentially carries the weight of the airguns plus most of the weight added to provide a small downward force or negative buoyancy. The buoyancy system also comprises the element 411 which is adjustable either remotely by an operator or automatically by a sensing and control system, to compensate for changes in forces.

From the above, it should be clear that much of the existing and well proven equipment used for surveys can be adapted for subsea applications by adding weight until the buoyancy is slightly negative, and an adjustable buoyancy control system to control the buoyancy, for example to level a cable at a predetermined depth.

Returning once more to the example of seismic surveys, a conventional streamer and airgun may be provided with added weight and adjustable buoyancy in the manner described. Once the mother vessel is out of the ice, the streamers may be towed behind the ship, and the survey continued in a conventional manner. Of course, similar transitions between a 'surface mode' and a 'subsea mode' may be practical for many surveys, not just seismic surveys.

FIG. 5 shows an embodiment wherein the mother vessel 100 is a submarine. In general, the submarine breaks less ice than the icebreaker in FIG. 1. Both the submarine and the icebreaker also save energy because one or more smaller vessel(s) is/are employed for much of the towing during a survey.

In the specific example of a seismic survey, power is required in order for the acoustic waves to penetrate, for example, a few km into a subterranean formation. This means that energy must be provided from the mother vessel in a form that allows quick release, and in a sufficient amount to allow repeated shots. Dynamite or other explosive charges need special handling, and they may have adverse effects on the environment, for example by killing fish. For these and other reasons, the preferred energy source is currently compressed air. On a surface vessel with ample deck space and free access to the atmosphere, the compressed air for charging the airguns may be supplied by large compressors when needed. Thus, a surface vessel does not need a large storage facility for compressed air.

The submarine illustrated in FIG. 5 does not have free access to the atmosphere when submerged. Hence, it may need to penetrate ice 501 with a snorkel 510 at regular intervals, and store the air in a storage tank 520 for later use in the airguns.

Figure 6:
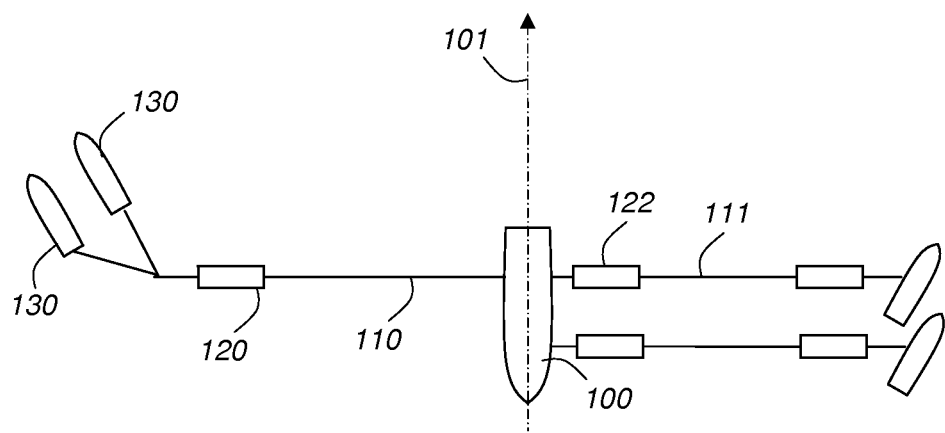
FIG. 6 corresponds to FIG. 1, and illustrates several vehicles per cable and several cables per side.

FIG. 6 illustrates that several subsurface towing vessels 130 can be connected to one conventional streamer 110, for example if one subsurface towing vessel 130 is unable to provide the power required. Some reference numerals are omitted from FIG. 6 for clarity.

FIG. 6 also illustrates an example where several conventional streamers 111 are extended from one side of a stationary mother vessel 100. In this example, a source 122 is kept near the vessel 100. However, providing a source 122 near the vessel 100 is not a requirement for deploying cables.

The rest of the elements on FIG. 6 correspond to similar elements found in FIG. 1 and discussed above. Of course, similar streamers can be deployed from both sides of the vessel 100. For example, up to 6 conventional survey cables could be deployed per side with 25 m spacing and out as far as 3 km per side. The cables could be deployed via chutes in the ships side under the ice level. The configuration would result in good quality data and a high rate of coverage.

The embodiments above are examples intended to clarify the invention, which is fully defined by the following claims.

The invention claimed is:

1. A method for surveying in ice covered waters from a non-towing vessel, comprising the steps of:
    attaching at least one survey cable to a non-towing mother vessel, the at least one survey cable having a proximate end and a distal end;
    connecting the distal end of the at least one survey cable to at least one subsurface towing vessel;
    extending at least one survey device to the at least one survey cable between the proximal end and the distal end of the at least one survey cable;
    deploying the at least one survey cable in a direction perpendicular to a longitudinal axis of the mother vessel so that the at least one survey device is forward of a stern of the non-towing mother vessel; and
    obtaining a measurement using the at least one survey device.

2. The method according to claim 1, further comprising the step of providing power to the survey device and/or the subsurface towing vessel in a form selected from a group comprising compressed gas, pressurized liquid and electricity.

3. The method according to claim 1, wherein extending the at least one survey cable involves moving the subsurface towing vessel away from the non-towing mother vessel in a first direction perpendicular to a longitudinal axis of the non-towing mother vessel, the method further comprising the steps of:
    moving the vessels a predetermined distance along the longitudinal axis;
    performing a measurement using the survey device; and
    moving the subsurface towing vessel towards the non-towing mother vessel in a direction opposite the first direction.

4. The method according to claim 1, wherein deploying the at least one survey cable involves moving the subsurface towing vessel along a path around the non-towing mother vessel.

5. The method according to claim 4, further comprising the steps of:
    moving the vessels a predetermined distance along the longitudinal axis; and
    obtaining a measurement using the survey device.

6. The method according to claim 1, further comprising the step of stopping the vessels before performing the measurements.

7. The method according to claim 1, wherein the subsurface towing vessel is controlled and/or powered by a separate umbilical.

8. The method according to claim 2, wherein extending the at least one survey cable involves moving the subsurface towing vessel away from the non-towing mother vessel in a first direction perpendicular to a longitudinal axis of the non-towing mother vessel, the method further comprising the steps of:
    moving the vessels a predetermined distance along the longitudinal axis;
    performing a measurement using the survey device; and
    moving the subsurface towing vessel towards the non-towing mother vessel in a direction opposite the first direction.

* * * * *